United States Patent
McLaughlin et al.

(10) Patent No.: US 10,052,086 B2
(45) Date of Patent: Aug. 21, 2018

(54) MEDICAL DEVICE FOR INSERTION INTO A MATERIAL TO OBTAIN A MATERIAL SAMPLE AND A METHOD THEREOF

(71) Applicant: The University of Western Australia, Crawley (AU)

(72) Inventors: Robert Ainsley McLaughlin, Bayswater (AU); Bryden Christopher Quirk, Mount Nasura (AU); Dirk Lorenser, Bull Creek (AU); Loretta Scolaro, Mt. Lawley (AU)

(73) Assignee: The University of Western Australia, Crawley (AU)

( * ) Notice: Subject to any disclaimer, the term of this patent is extended or adjusted under 35 U.S.C. 154(b) by 0 days.

(21) Appl. No.: 15/116,498

(22) PCT Filed: Jan. 30, 2015

(86) PCT No.: PCT/AU2015/000051
§ 371 (c)(1),
(2) Date: Aug. 3, 2016

(87) PCT Pub. No.: WO2015/113113
PCT Pub. Date: Aug. 6, 2015

(65) Prior Publication Data
US 2017/0188999 A1     Jul. 6, 2017

(30) Foreign Application Priority Data
Feb. 3, 2014  (AU) ................................. 2014900312

(51) Int. Cl.
*A61B 6/00*     (2006.01)
*A61B 10/02*    (2006.01)
*A61B 5/00*     (2006.01)

(52) U.S. Cl.
CPC ........ *A61B 10/0275* (2013.01); *A61B 5/0086* (2013.01); *A61B 5/4064* (2013.01)

(58) Field of Classification Search
None
See application file for complete search history.

(56) References Cited

U.S. PATENT DOCUMENTS 5,251,641 A * 10/1993 Xavier ............... A61B 10/0266
600/567
5,467,767 A    11/1995 Alfano et al.
(Continued)

FOREIGN PATENT DOCUMENTS

JP     2005-118134 A    5/2005
WO     2004052210 A1    6/2004
(Continued)

OTHER PUBLICATIONS

International Preliminary Report on Patentability dated Jan. 14, 2016, issued in corresponding Application No. PCT/AU2015/000051, filed Jan. 30, 2015, 14 pages.
(Continued)

*Primary Examiner* — Joel F Brutus
(74) *Attorney, Agent, or Firm* — Christensen O'Connor Johnson Kindness PLLC (57) ABSTRACT

The invention relates to a medical device for obtaining a material sample from a material. The medical device comprises a first member comprising a receptacle for receiving the material sample; and a second member having a hollow region for accommodating at least a portion of the first member such that the at least a portion of the first member is movable within the second member. The first and second members are arranged such that when the material sample is received in the receptacle of the first member, the material sample can be obtained by moving the first member within the second member. The medical device further comprises (Continued)

an optical element arranged to receive electromagnetic radiation that can be used to determine information in relation to the material. The medical device has a distal end for inserting the medical device into the material. The distal end further comprises an inlet that is transmissive for at least the received electromagnetic radiation and that is spaced apart from the receptacle of the first member. The medical device is arranged such that the optical element receives the electromagnetic radiation through the inlet.

20 Claims, 8 Drawing Sheets

(56) References Cited

U.S. PATENT DOCUMENTS

| | | | |
|---|---|---|---|
| 6,059,734 A * | 5/2000 | Yoon | A61B 10/0275 600/565 |
| 6,231,514 B1 | 5/2001 | Lowe et al. | |
| 6,564,087 B1 | 5/2003 | Pitris et al. | |
| 7,736,301 B1 * | 6/2010 | Webler | A61B 5/0062 385/53 |
| 2005/0203419 A1 * | 9/2005 | Ramanujam | A61B 5/0075 600/473 |
| 2007/0167736 A1 * | 7/2007 | Dietz | A61B 10/0275 600/411 |
| 2008/0132805 A1 | 6/2008 | Heywang-Koebrunner et al. | |
| 2009/0048610 A1 * | 2/2009 | Tolkowsky | A61B 90/11 606/130 |
| 2011/0021948 A1 * | 1/2011 | Lee | A61B 10/0275 600/567 |
| 2013/0267776 A1 | 10/2013 | Brennan et al. | |

FOREIGN PATENT DOCUMENTS

| | | |
|---|---|---|
| WO | 2006095343 A1 | 9/2006 |
| WO | 2008144831 A1 | 12/2008 |
| WO | 2010058344 A1 | 5/2010 |
| WO | 2013067595 A1 | 5/2013 |
| WO | 2013091090 A1 | 6/2013 |
| WO | 2013/157006 A1 | 10/2013 |
| WO | 2014132110 A1 | 9/2014 |
| WO | 2015010213 A1 | 1/2015 |

OTHER PUBLICATIONS

International Search Report dated Apr. 9, 2015, issued in corresponding Application No. PCT/AU2015/000051, filed Jan. 30, 2015, 5 pages.

Extended European Search Report dated May 26, 2017, issued in corresponding European Application No. EP 15 74 3666, filed Jan. 30, 2015, 8 pages.

Notification of Reasons for Refusal, dated May 8, 2018, issued in corresponding Japanese Patent Application No. 2016-567106, filed Mar. 30, 2017, 18 pages.

* cited by examiner

MEDICAL DEVICE FOR INSERTION INTO A MATERIAL TO OBTAIN A MATERIAL SAMPLE AND A METHOD THEREOF

FIELD OF THE INVENTION

The present invention broadly relates to a medical device and a method for obtaining a material sample from a material, and relates particularly, not exclusively though, to a biopsy needle for obtaining a tissue sample from biological tissue.

BACKGROUND OF THE INVENTION

The determination of the presence or extent of diseased tissue is important in a range of procedures in medicine and biology. For example, the assessment of malignant tissue is important for the treatment of cancer. A biopsy needle is inserted into the tissue in question to obtain a sample of the tissue such that it can be examined for cancerous cells. An exemplary conventional biopsy needle has a hollow compartment near the tip of the needle to receive the tissue sample, and a cutting blade to cut the tissue sample that is located within the compartment from surrounding tissue. Some biopsy needles may also apply suction to the tissue to pull the tissue sample into the compartment, as is often done in brain biopsies.

A number of problems exist in needle biopsy procedures. For example, it is important to position the biopsy needle to obtain the optimal tissue sample. Specifically, when extracting a tissue sample from cancerous tissue, it is important to obtain the sample from an area containing malignant cells rather than fat or necrotic cells. Additionally, it is important to avoid damaging other physiological structures such as blood vessels.

SUMMARY OF THE INVENTION

In accordance with a first aspect of the present invention, there is provided a medical device for obtaining a material sample from a material, the medical device comprising:
  a first member comprising a receptacle for receiving the material sample;
  a second member having a hollow region for accommodating at least a portion of the first member such that the at least a portion of the first member is movable within the second member; and
  an optical element arranged to receive electromagnetic radiation that can be used to determine information in relation to the material;
  wherein the medical device has a distal end for inserting into the material, the distal end comprising an inlet that is transmissive for at least the radiation that is received by the optical element and that is spaced apart from the receptacle of the first member, and
  wherein the first and second members are arranged such that, when the material sample is received in the receptacle of the first member, the material sample can be obtained from the material by moving the first and second members relative to each other.

Embodiments of the invention have significant advantages. In particular, when the medical device is inserted into the material from which the material sample is to be obtained, an optimal region can be located for obtaining the material sample. Specifically, by receiving electromagnetic radiation that is backscattered or emitted from a material region when the medical device is inserted into the material, information in relation to that material region can be obtained. For example, it can be determined whether the material region contains diseased cells such as cancerous cells or rather fat cells and necrotic cells. The information may also be used to characterise the diseased tissue, such as identifying the grade or severity of an area of malignant tissue. Also, other physiological structures such as blood vessels may be located so that damage to such structures by the medical device can be avoided.

For the ease of understanding, the term "diseased" is used throughout the patent specification as a synonym for an abnormality in the tissue including a lesion or a tumour that may be benign, pre-malignant or malignant.

Furthermore, by providing an inlet through which the electromagnetic radiation is received that is spaced apart from the receptacle, the medical device provides an improved degree of freedom regarding the position and number of inlets. This results in a more versatile medical device with which material regions in different directions can be assessed. In particular, a medical device may be provided which enables obtaining three dimensional images of a material region. Also, by providing an inlet that is spaced apart from the receptacle, it may be possible to manufacture the distal end of the medical device in a relatively rigid manner. This may have an advantage in particular applications in which the medical device is inserted into relatively stiff tissue. Furthermore, a separate inlet can be manufactured in a relatively simple manner, for example by the use of a laser. In this regard, it may be possible to retrofit the optical element and the inlet to a conventional biopsy needle. Moreover, by separating the receptacle from the inlet, the optical element may never be in proximity of the material sample that is collected in the receptacle. This has significant advantages in relation to sterilisation of the medical device.

The medical device typically is elongate. In one embodiment, the medical device is a medical needle such as a biopsy needle for insertion into biological tissue to obtain a tissue sample. The tissue sample may comprise diseased tissue such as cancerous tissue. In embodiments in which the medical device is a biopsy needle, the first member typically is an inner needle and the second member is a hollow outer needle.

The medical device typically is arranged such that the optical element receives the electromagnetic radiation from a material region that is adjacent to the medical device when the medical device is inserted into the material. For example, the material region may be located at a side and/or front portion of the medical device. In this regard, the inlet is located at a side portion of the distal end of the medical device.

The received electromagnetic radiation may originate from the tissue by a range of different mechanisms. For example, the electromagnetic radiation may be backscattered from the material region and/or fluorescently emitted from the material region and/or emitted by luminescence from the material region. By receiving the electromagnetic radiation from the material region, information may be obtained in relation to the material region, for example in form of an image of the material region, and/or in the form of measurements of optical properties of the material region. The obtained information may indicate whether the material region contains malignant cells, fat cells or necrotic cells, or other tissue types. It may also be used to characterise the diseased tissue, such as identifying the grade of malignant cells. Based on the obtained information, a desired material sample may be located.

The medical device may be arranged such that the optical element receives the electromagnetic radiation through the inlet from a direction that is substantially parallel to a central axis of the medical device. In this way, information in relation to the material may be obtained in a forward facing direction when the medical device is advanced into the material. Additionally or alternatively, the medical device may be arranged such that the optical element receives the electromagnetic radiation through the inlet from a direction that is non-parallel to the central axis of the medical device. For example, the medical device may be arranged such that the optical element receives the electromagnetic radiation through the inlet from a direction that is substantially perpendicular to the central axis of the medical device. A person skilled in the art will appreciate that any suitable angle relative to the central axis of the medical device is envisaged.

The optical element may further be arranged to direct electromagnetic radiation into the material. The electromagnetic radiation may have any suitable wavelength. In one particular example, the electromagnetic radiation is infrared light such as near-infrared light. The near-infrared light may for example have a wavelength in the range from 0.7 micrometers to 3 micrometers.

The medical device may be arranged such that the optical element receives the electromagnetic radiation from and/or directs the electromagnetic radiation in a plurality of directions.

The optical element may comprise an optical fibre for transmitting the electromagnetic radiation. The optical fibre may be connected to at least one of: an optical processing system, and a light source and a detector.

The medical device typically is arranged such that the receptacle of the first member receives the material sample from a material region that is located at a side portion of the medical device when the medical device is inserted into the material. In this regard, the receptacle is typically arranged at a side portion of the first member. The size of the receptacle typically defines the size of the material sample.

In embodiments of the invention, the medical device is arranged such that the first member is rotatable within the second member. The first member is typically rotatable about a longitudinal axis of the medical device.

Additionally or alternatively, the medical device is arranged such that the first member is translatable within the second member. The first member is typically translatable along the longitudinal axis of the medical device. For example, the first and second members may have generally tubular shape. The second member may have a portion that has an inner diameter and the first member may have a portion that has an outer diameter such that there is a sliding fit of the first member within the second member.

The first member may be movable within the second member between an imaging configuration in which the optical element receives the electromagnetic radiation through the inlet, and a sampling configuration in which the receptacle receives the material sample. The first member may be rotatable and/or translatable between the sampling configuration and the imaging configuration. In a specific example, the first member is rotated within the second member about substantially 180 degrees to move between the imaging configuration and the sampling configuration. A person skilled in the art will appreciate that any suitable angles are envisaged such as 45 degrees, 90 degrees and 135 degrees. The second member may comprise a sampling aperture that is arranged to align with the receptacle of the first member when the first member is in the sampling configuration. The sampling aperture typically is of similar size or larger as the size of the receptacle. In this way, the material sample can be passed through the sampling aperture of the second member to be received in the receptacle of the first member.

The medical device may be arranged such that when the receptacle receives the material sample, the material sample can be obtained by rotating the first member within the second member. Additionally or alternatively, the medical device may be arranged such that the material sample can be obtained by translating the first member within the second member. Specifically, the first member and/or the second member may have a cutting element. For example, the cutting element may be arranged at an edge of the receptacle of the first member and/or at an edge of the sampling aperture of the second member.

In one embodiment, the material sample is drawn into the receptacle by application of a force such as by virtue of suction. For example, the first member may comprise a hollow or tubular region such that suction can be applied to the hollow or tubular region of the first member.

When the first member is in the imaging configuration, a portion of the second member may at least partially cover the receptacle of the first member. Additionally or alternatively, the or another portion of the second member may at least partially cover the optical element when the first member is in the sampling configuration. For example, the second member may have a tubular shape such that a wall portion of the second member covers the optical element when the first member is in the sampling configuration and/or the receptacle when the first member is in the imaging configuration.

The medical device may comprise an indicator that is arranged to indicate a position of the first member relative to the second member. Specifically, the indicator may indicate the imaging configuration and/or the sampling configuration. In this way, an operator of the medical device can control the movement of the first member within the second member.

The distal end of the medical device may be closed. The medical device may comprise a closure element such as a closed end cap that can be attached to the distal end of the medical device. For example, both distal ends of the first and second members may be closed. Alternatively, a distal end of the first member may be closed, and a distal end of the second member may be open.

The distal end of the medical device may have a pointed or a blunt tip. For example, for applications in the brain, it may be advantageous to provide a medical device having a blunt tip for inserting the medical device into brain tissue to avoid puncturing blood vessels in the brain. For other applications, it may be advantageous to have a pointed tip to ease insertion of the device into tissue.

In a specific embodiment, the inlet is arranged distally relative to the receptacle of the first member when the medical device is inserted into the material. For example, the inlet may be arranged at or within the tip of the distal end of the medical device. In this way, information in relation to the material region can be captured directly in front of the receptacle when the medical device is advanced into the material.

The inlet may comprise an outer inlet at a distal end of the second member. Additionally or alternatively, the inlet may comprise an inner inlet at a distal end of the first member. In one example, the medical device is arranged such that the inner inlet and the outer inlet can be aligned by moving the first member within the second member.

In one embodiment, the inlet is also spaced apart from the sampling aperture of the second member that can be aligned with the receptacle. Specifically, the outer inlet may be spaced apart from the sampling aperture.

The inlet may be in the form of an aperture. Additionally or alternatively, the inlet may comprise a material that is transmissive to at least the received electromagnetic radiation, for example glass or a polymeric material such as plastic. In one particular example, the inlet may be in the form of a window. The inlet may be arranged such that an outer surface of the first member and/or the second member is flush.

The inlet may have any suitable shape. For example, the outer inlet may be in the form of a transverse slit at the distal end of the second member. Thus, by moving the optical element relative to the second member, imaging of a two dimensional area may be enabled.

In a specific embodiment, the inlet is formed by the tip of the distal end of the medical device. In particular, the tip may be made of a material that is transmissive for at least the received electromagnetic radiation, for example glass or a polymeric material such as plastic. In this way, imaging of a three dimensional region may be enabled.

The distal end of the medical device may comprise a plurality of inner inlets and/or a plurality of outer inlets. For example, if the distal end of the second member comprises a plurality of outer inlets, the optical element may be moveable relative to the second member such that electromagnetic radiation can be directed into and/or received from more than one outer inlet.

In one embodiment, the optical element is arranged within an inner portion of the first member. The optical element may for example be attached to an inner portion of the first member.

In some embodiments, the inner inlet of the first member is arranged substantially opposite to the receptacle. In this way, the first member is rotatable relative to the second member about substantially 180 degrees to move between the sampling configuration and the imaging configuration.

In accordance with a second aspect of the present invention, there is provided a method of obtaining a material sample from a material, the method comprising the steps of:
providing the material;
providing a medical device that may be in accordance with the first aspect of the invention;
inserting the distal end of the medical device into the material;
emitting electromagnetic radiation into the material;
receiving electromagnetic radiation in response to the emitted electromagnetic radiation, the received electromagnetic radiation being usable for determining information in relation to the material;
receiving the material sample within the receptacle of the first member; and
moving the first and second members relative to each other to obtain the material sample from the material.

In one specific embodiment, the method comprises a step of moving the first member relative to the second member from the imaging configuration to the sampling configuration. This step may be conducted by rotating and/or translating the first member within the second member.

The step of obtaining the material sample may comprise cutting the material sample from surrounding material. The step of cutting the material may comprise rotating and/or translating the second member relative to the first member.

In one particular example, the emitted electromagnetic radiation is infrared light such as near-infrared light.

The method may comprise a step of analysing the received electromagnetic radiation. For example, the received electromagnetic radiation may be analysed by a suitable imaging technique such as optical coherence tomography and/or fluorescence microscopy. Based on the analysis of the received electromagnetic radiation, the material sample may be identified and/or mechanical or optical properties of the material may be determined, such as an elasticity of the material.

The invention will be more fully understood from the following description of specific embodiments of the invention. The description is provided with reference to the accompanying drawings.

DETAILED DESCRIPTION OF SPECIFIC EMBODIMENTS

Embodiments of the present invention relate to a medical device for insertion into a material to obtain a material sample. The medical device may be a medical needle such as a biopsy needle for obtaining a sample of biological tissue. Exemplary biopsy needles are used for different applications such as for breast biopsies, prostate biopsies, brain biopsies, liver biopsies, and muscle biopsies.

The medical device comprises a first member with a receptacle that is arranged to receive the material sample. The receptacle is typically arranged such that the material sample is received from a material region that is located at a side portion of the medical device when the medical device is inserted into the material. In addition, the medical device comprises a second member that has a hollow region for accommodating at least a portion of the first member such that the at least a portion of the first member is movable within the second member. For example, the first member may be an inner needle that comprises a receptacle for accommodating the sample of biological tissue, and the second member may be an outer needle that has a tubular shape. In this example, the inner needle is rotatable and translatable within the outer needle. Such core biopsy needles are well known in the art and find applications in various fields, such as for examining cancerous tissue.

The medical device in accordance with embodiments of the invention further comprises an optical element that is arranged to receive electromagnetic radiation. The optical element may receive the electromagnetic radiation in response to electromagnetic radiation emitted into a material region that is adjacent to the medical device when the medical device is advanced into the material. However, alternatively the material region may emit electromagnetic radiation that is received by the optical element. In this way, information in relation to the material region can be obtained. For example, the obtained information may be indicative of a location of physiological structures such as blood vessels, or of a type of the tissue such as whether the tissue region contains cancerous cells, necrotic cells, fat cells or other normal healthy cells. As a further example, the information may characterise the tissue region, such as indicating the grade of malignant cells. Based on the obtained information, a desired tissue sample may be located.

An inlet is arranged at a distal end of the medical device such that when the medical device is inserted into the material, the optical element receives the electromagnetic radiation through the inlet. The inlet is transmissive for the electromagnetic radiation and spaced apart from the receptacle of the first member. This has significant advantages that a certain amount of freedom is provided regarding the position and number of inlets. This results in a more versatile medical device with which material regions in different directions can be assessed. Furthermore, by providing an inlet that is spaced apart from the receptacle, the configuration of the medical device can be simplified and thereby also the manufacturing process. Also, it may be possible to manufacture the distal end of the medical device in a relatively rigid manner which has advantages in certain applications in which the material such as biological tissue is relatively stiff.

Figure 1:
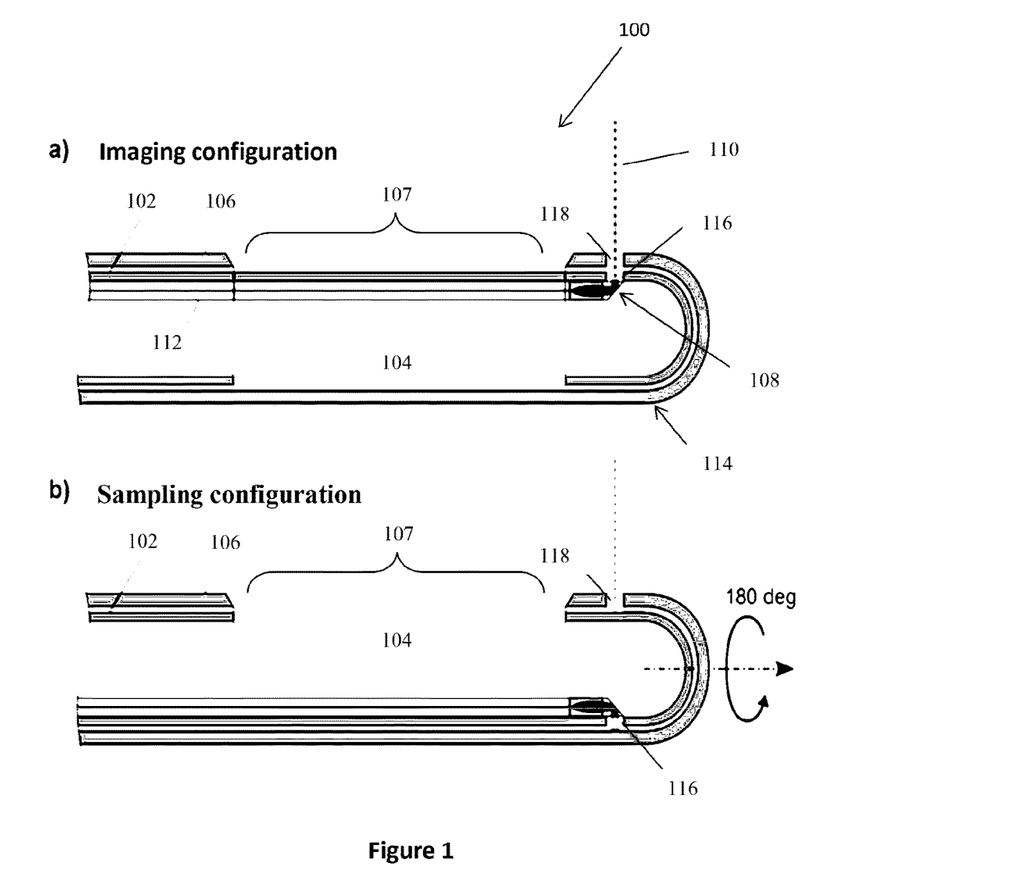
FIG. 1 is a schematic representation of a medical device for insertion into a material to obtain a material sample in accordance with an embodiment of the present invention.

Referring now to FIG. 1, there is shown a medical device 100 in accordance with a specific embodiment of the present invention. In this particular embodiment, the medical device is a brain biopsy needle 100 that can be configured in two positions, i.e. an imaging configuration as shown in FIG. 1a and a sampling configuration as shown in FIG. 1b.

In particular, the brain biopsy needle 100 comprises an inner needle 102 having a receptacle 104 for receiving a sample of brain tissue, and an outer needle 106 that has a tubular shape such that it can accommodate at least a portion of the inner needle 102. The inner needle 102 is rotatable and translatable within the outer needle 106. Specifically, the inner needle 102 is rotatable about the central axis of the brain biopsy needle 100 within the outer needle 106 to move between the imaging configuration and the sampling configuration.

The brain biopsy needle 100 further comprises an optical element 108 that is arranged to direct electromagnetic radiation 110 into a tissue region. In this particular example, near-infrared light 110 is emitted into the brain tissue region. The optical element 108 is also arranged to receive light that is back-scattered by the biological tissue in response to the emitted near-infrared light 110. Thereby, information in relation to the tissue region can be obtained. A person skilled in the art will appreciate that the emitted electromagnetic radiation can be electromagnetic radiation of any suitable wavelength such as visible light, infrared light and ultraviolet light. The near-infrared light 110 directed into the tissue region propagates into the tissue region and a portion of the light 110 is back-scattered by the tissue. For near-infrared light, the maximum distance into biological tissue, from which backscattered light can be detected to form an image, is approximately 2-3 mm. The distance of the emitted light determines the imaging field of view.

In this particular example, the optical element 108 comprises an optical fibre 112 that is connected to a light source (not shown) and an optical processing system (not shown). The optical processing system in this particular example may be an imaging scanner such as an optical coherence tomography (OCT) scanner, or a fluorescence scanner. However, a person skilled in the art will appreciate that the optical processing system may use any suitable optical imaging technique such as an OCT measurement with a simultaneous fluorescence measurement such as with a fluorescent agent protoporphyrin IX, OCT alone, fluorescence alone, multi-photon microscopy, diffuse optical tomography, total internal reflection fluorescence microscopy, phase contrast microscopy, stimulated emission depletion microscopy, near-field scanning optical microscopy, differential interference contrast microscopy, second harmonic imaging microscopy, reflectance spectroscopy and Raman spectroscopy.

Further, a person skilled in the art will appreciate that the medical device may be arranged to obtain multiple measurements. In this way, information indicative of a movement of the tissue may be determined that enables determination of a mechanical property of the tissue region such as elasticity. An example for the determination of a mechanical property of tissue is described in International Patent Application No. PCT/AU2012/001385 which is herein incorporated in its entirety by reference.

In this embodiment, the brain biopsy needle 100 has a closed distal end 114 terminating in a blunt tip. A blunt tip has significant advantages in the field of brain biopsies in that when the brain biopsy needle 100 is inserted into brain tissue, it is less likely that the tip of the brain biopsy needle 100 will puncture any blood vessels in the brain. In this particular example, the distal end of the inner needle 102 is fully enclosed within the distal end of the outer needle 106 and both needles 102, 106 have respective closed distal ends.

The brain biopsy needle 100 further comprises an inlet that is arranged at the distal end 114, between the blunt tip of the brain biopsy needle and the receptacle 104. In this embodiment, the inlet comprises an inner inlet 116 arranged at the distal end of the inner needle 102, and an outer inlet 118 arranged at the distal end of the outer needle 106. The inner and outer inlets 116, 118 comprise respective apertures that are transmissive for the light 110 that is directed into the tissue region and received by the optical element 108. In this particular example, at least the outer inlet 118 comprises a glass material within the aperture such that the outer surface of the outer needle 106 is flush. Other transmissive materials may also be used to form the inlet, for example polymeric materials such as optical adhesive or plastic. This provides significant advantages for inserting and cleaning the brain biopsy needle 100.

In this embodiment, the inner inlet 116 is aligned with the outer inlet 118 when the brain biopsy needle 100 is in the imaging configuration. The outer and inner inlets 116, 118 are sized and positioned in a corresponding manner so that when the brain biopsy needle 100 is configured in the imaging configuration, light can be emitted and received through the inlets 116, 118 without any substantive loss of information.

The inner inlet 116 is located substantially opposite relative to the receptacle 104 such that the inner needle 102 is rotated about substantially 180 degrees to move between the imaging configuration and the sampling configuration. This has the advantage that the optical fibre 112 can be attached to an inner wall of a hollow region of the inner needle 102. However, a person skilled in the art will appreciate that the optical fibre 112 may alternatively be arranged at or within the outer needle. For example, the hollow region of the outer needle may have a channel that comprises the optical fibre.

The inner inlet 116 is spaced apart from the receptacle 104 and the outer inlet 118 is spaced apart from a corresponding sampling aperture 107. By providing a separate inlet, significant advantages can be provided as mentioned previously.

During insertion of the brain biopsy needle 100 into the brain tissue, the brain biopsy needle 100 is configured in the imaging configuration as shown in FIG. 1a.

Specifically, the inner inlet 116 of the inner needle 102 and the outer inlet 118 of the outer needle 106 are aligned such that electromagnetic radiation can be directed into the tissue region and received by the optical element 108 through the inlets 116, 118. In addition, the receptacle 104 is covered by a wall portion of the outer needle 106.

In this particular example, the near infrared light 110 is emitted in and received from a direction that is substantially perpendicular to the central axis of the brain biopsy needle 100. In this way, information can be obtained in relation to a tissue region that is substantially the same tissue region from which the tissue sample is extracted. In particular, by positioning the inlet 116 separately and distally relative to the receptacle 104, information of the tissue region can be obtained directly in front of the receptacle 104 when the brain biopsy needle 100 is advanced into the tissue.

However, a person skilled in the art will appreciated that the brain biopsy needle 100 may be arranged such that electromagnetic radiation is emitted in and received from a direction that is parallel to the central axis of the brain biopsy needle. In this way information from a tissue region may be obtained that is located in front of the brain biopsy needle when the brain biopsy needle is advanced into the biological tissue. Moreover, the optical element 108 may direct electromagnetic radiation into and/or receive electromagnetic radiation from any suitable direction or directions relative to the central axis of the brain biopsy needle such as 30 degrees, 45 degrees and 135 degrees.

By providing the optical element 108 and the inner and outer inlets 116, 118 within the tip of the brain biopsy needle 100, a desired tissue sample may be located and obtained without the need for further movement of the brain biopsy needle 100 into the brain tissue. The brain biopsy needle 100 may remain at its position within the brain tissue and the inner needle 102 merely requires to be rotated to move from the imaging configuration into the sampling configuration as shown in FIG. 1b. This has the significant advantage that the movement of the brain biopsy needle 100 within the brain tissue can be minimised.

It should be noted that the optical element 108 and the inner inlet 116 may be positioned such that the near infrared light 110 can be directed into and received from the tissue region through the sampling aperture 107. As a consequence, the outer inlet 118 of the outer needle 106 may not be necessary.

Once the brain biopsy needle 100 is advanced into the brain tissue to a desired position, the inner needle 102 is rotated about substantially 180 degrees to position the brain biopsy needle 100 in the sampling configuration as shown in FIG. 1b. Specifically, when the inner needle 104 is positioned in the sampling configuration, the sampling aperture 107 of the outer needle 106 is aligned with the receptacle 104 such that a tissue sample can pass through the sampling aperture 107 and be contained within the receptacle 104. In addition, a wall portion of the outer needle 106 covers the optical element 108 and the inner inlet 116.

In this particular embodiment, a force in form of suction is applied to a hollow region of the inner needle 102 to aspirate tissue into the receptacle 104. Once sufficient tissue is received within the receptacle 104, the tissue sample can be cut from surrounding tissue by rotating the inner needle 102 within the outer needle 106. Simultaneously, the outer needle 106 occludes the receptacle 104. The outer needle comprises a cutting element (not shown) located at the longitudinal edge of the sampling aperture 107 and as the inner needle 102 is rotated within the outer needle 106, the cutting element cuts through the tissue thereby obtaining the tissue sample for further analysis. The inner needle 102 can then be retracted either separately from or together with the outer needle 106.

A person skilled in the art will appreciate that the tissue sample may be cut from surrounding tissue by alternatively or additionally translating the inner needle within the outer needle. In this regard, the outer needle may for example comprise a cutting element on a transversal edge of the sampling aperture.

The brain biopsy needle 100 further comprises an indicator (not shown) for indicating a position of the inner needle 102 relative to the outer needle 106. Specifically, the indicator may indicate the imaging configuration shown in FIG. 1a and the sampling configuration shown in FIG. 1b. The indicator may assist an operator to control the movement of the inner needle 102 within the outer needle 106. The indicator may be implemented in any suitable manner.

In accordance with a further embodiment of the present invention (not shown), a biopsy needle such as the brain biopsy needle 100 comprises an optical element similar to the optical element 108. Rather than emitting light into the tissue in a direction that is substantially perpendicular to the central axis of the biopsy needle 100, the light is emitted into the tissue in a direction that is parallel to the central axis of the biopsy needle. In other words, light is emitted in a forward direction when the biopsy needle is advanced into the tissue. Consequently, backscattered light is received by the optical element from a tissue region that is located substantially in front of the tip of the biopsy needle.

Specifically, the inner inlet 116 and the outer inlet 118 may be located within the tip of the distal end of the inner and outer needle, respectively. With such arrangement, it may not be necessary to rotate the inner needle within the outer needle to move between the imaging configuration and the sampling configuration. Also, this arrangement may enable continuous imaging of the material directly in front of the distal end of the biopsy needle. For example, blood vessels and other physiological structures may be located immediately ahead of the tip of the biopsy needle.

In a further exemplary embodiment, there is provided a biopsy needle such as the brain biopsy needle 100 that comprises an inlet which has a plurality of outer inlets. This enables receiving electromagnetic radiation from more than one position and direction. In this case, the optical element may be movable relative to the outer inlet, for example by rotating the inner needle if the optical element is affixed to the inner needle. Alternatively, the biopsy needle may comprise a plurality of optical elements. In one specific example, light is emitted through one outer inlet whilst light that is backscattered and/or fluorescently emitted from the tissue is received through another inlet.

Additionally or alternatively, the outer inlet has a larger size than the inner inlet or an imaging view of the optical element. For example, the outer inlet may be in form of a slit and the optical element may be movable relative to the slit such that electromagnetic radiation can be received from a range of angles. In this way, imaging of a two dimensional area may be enabled. In an alternative example, the outer inlet is formed by the tip of the distal end of the outer needle. The tip may be composed of a material that is transmissive to the electromagnetic radiation, such as glass. If the optical element is movable relative to the glass tip, imaging of a three dimensional region may be enabled.

A person skilled in the art will appreciate that the aforementioned features may not only apply to brain biopsy needles but to any suitable medical devices for insertion into material to obtain a material sample.

Figure 2:
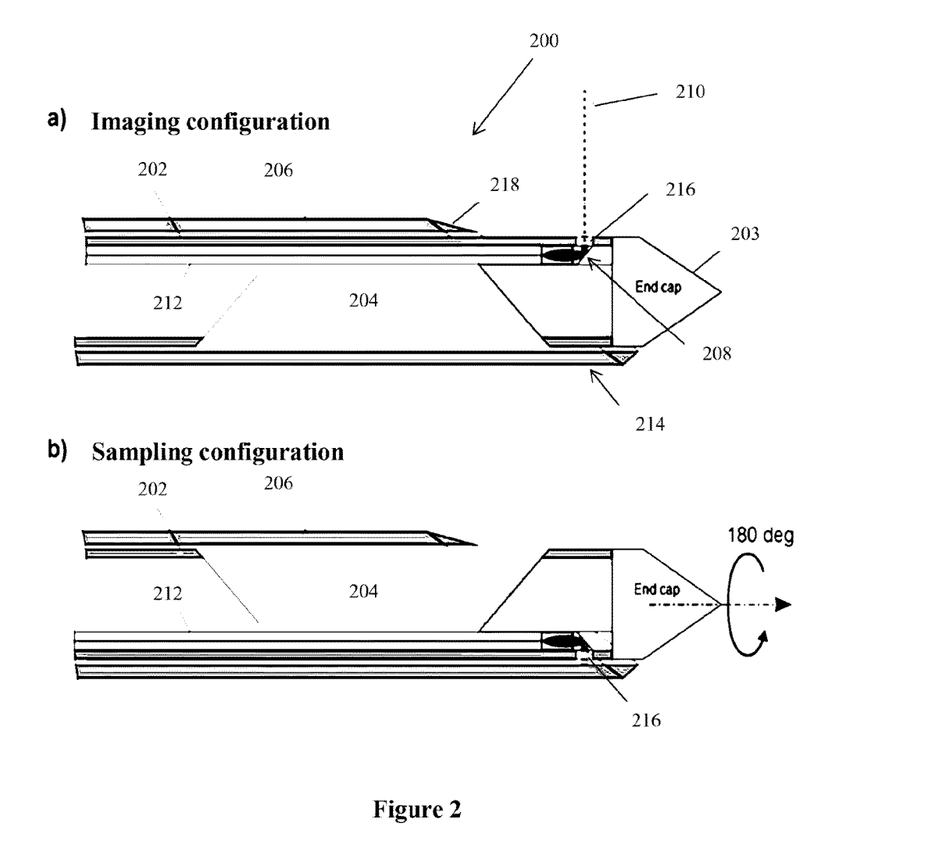
FIG. 2 is a schematic representation of a medical device in accordance with a further embodiment of the present invention.

Referring now to FIG. 2, there is shown a biopsy needle 200 in accordance with a further embodiment of the present invention. Similar to the embodiment shown in FIG. 1, the medical device is a biopsy needle 200 comprising an inner needle 202 having a receptacle 204 for receiving a sample of biological tissue, and an outer needle 206 that has a tubular shape such that it can accommodate at least a portion of the inner needle 202. The inner needle 202 is rotatable and translatable within the outer needle 206.

The biopsy needle 200 also comprises an optical element 208 that is arranged to direct near-infrared light 210 into a tissue region that is at a side portion of the biopsy needle 200 when the biopsy needle 200 is advanced into and/or retracted from the biological tissue. Similar to the embodiment shown in FIG. 1, the optical element 208 is arranged to receive light that is back-scattered by the biological tissue in response to near-infrared light 210 being directed into the biological tissue. The optical element 208 comprises an optical fibre 212 that is connected with a light source and an optical processing system (not shown).

The inner needle 202 comprises an inner inlet 216 similar to inlet 116 of the inner needle 102 shown in FIG. 1. The inner inlet 216 is transmissive for the near-infrared light 210 that is directed into and received from the tissue region by the optical element 208. Furthermore, the inner inlet 216 is spaced apart from the receptacle 204. By providing an inlet 216 that is separate to the receptacle 204, the inner inlet can be positioned within the tip such as within an end cap 203 of the inner needle 202. The end cap 203 that is positioned within an inner portion of the open distal end of the inner needle 202 may be replaceable. Thus, if the optical element 208 is positioned within the end cap, the optical element 208 may also be replaceable. In this way, the optical element 208 including the optical fibre 212 may be retrofitted into a conventional biopsy needle.

In contrast to the brain biopsy needle 100 shown in FIG. 1, the distal end of the inner needle 202 terminates with a sharpened tip which extends beyond the outer needle 206 when the biopsy needle 200 is inserted into the biological tissue. The outer needle 206 has an open distal end 214 and can be retracted to reveal the inner needle 202. An advantage of the use of a sharpened tip is that it allows easier penetration of the biopsy needle 200 into biological tissue. However, a disadvantage of a sharpened tip is that the tip extends beyond the tissue region from which the tissue sample is obtained. In some delicate organs, such as the brain, this may increase the risk of puncturing critical structures such as blood vessels. In such situations, the blunt tip as shown for the brain biopsy needle 100 may be preferable.

The biopsy needle 200 is inserted into the tissue with the receptacle 204 of the inner needle 202 retracted into the outer needle 206 such that the receptacle 204 is covered by a wall portion of the outer needle 206. The optical element 208 is affixed within the inner needle 202 so as to not occlude the receptacle 204, preferably substantially opposite to the receptacle 204 of the inner needle 202. However, other suitable arrangements are envisaged. For example, the optical element 208 may be positioned adjacent to the receptacle 204.

Similar to the brain biopsy needle 100, the biopsy needle 200 can be configured in an imaging configuration as shown in FIG. 2a and a sampling configuration as shown in FIG. 2b. When the biopsy needle 200 is positioned in the imaging configuration, the optical element can receive backscattered light 210 through the inner inlet 216. In this embodiment, it is not necessary to have an outer inlet in the outer needle 206. Instead, the distal end 214 of the outer needle 206 is angled thereby revealing the inlet 216 and the optical element 208 whilst the biopsy needle is in the imaging configuration. The distal end 214 of the outer needle 206 is angled in a manner such that in the imaging configuration, a wall portion of the outer needle 206 still occludes the receptacle 204.

Once the biopsy needle 200 is positioned within the tissue as desired, the inner needle 202 is first rotated, and the outer needle 206 is then retracted to reveal the receptacle 204 for receiving a tissue sample. Tissue will then be collected in the receptacle 204. At this position, a wall portion of the outer needle 206 covers the optical element 208 and the inner inlet 216. A person skilled in the art will appreciate that the distal end of the outer needle 206 may be angled in a manner such that the receptacle 204 is revealed by solely rotating the inner needle 202 within the outer needle 206. Thus, a retraction of the outer needle 206 may not be required.

The outer needle 206 is then advanced and/or rotated to cover the receptacle 204. The sharp cutting edge 218 of the outer needle 206 will sever any tissue that is inside the receptacle 204. Consequently, the tissue sample will be obtained. The inner needle 202, and possibly the outer needle 206, is then retracted from the tissue and the tissue sample may be extracted for further analysis.

Figure 3:
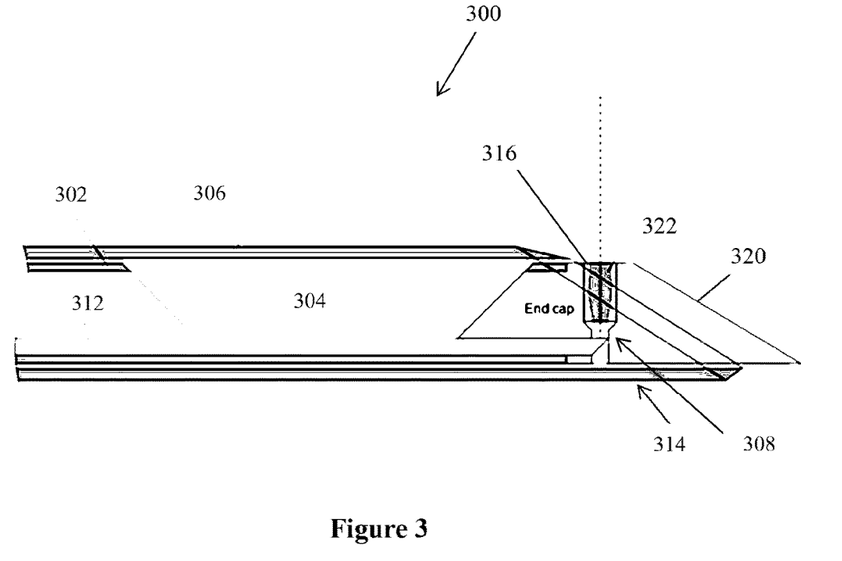
FIG. 3 is a schematic representation of a medical device in accordance with an embodiment of the present invention.

Referring now to FIG. 3, there is shown a further biopsy needle 300 in accordance with an embodiment of the invention. The biopsy needle 300 also comprises an inner needle 302 having a receptacle 304 for receiving a tissue sample. The receptacle 304 is terminated by an end cap 320 which in this particular example is sharpened.

Similar to the embodiment shown in FIG. 2, the biopsy needle 300 comprises an optical element 308 that is positioned within the end cap 320 of the distal end of the inner needle 302. The optical element 308 is arranged to direct and receive electromagnetic radiation through an inlet 316 from a tissue region that is located at a side portion of the biopsy needle 300. The optical element 308 comprises an optical fibre 312 and focusing optics 322 that are affixed within the inner needle 302 and that terminate in the end cap 320. A channel is created in the end cap 320 into which the optical fibre 312 is positioned. The proximal end of the optical fibre 312 terminates in an optical scanning machine (not shown), such as an optical coherence tomography (OCT) scanner, or a fluorescence scanner.

The biopsy needle 300 further comprises an outer needle 306 having a tubular shape to accommodate the inner needle 302. However, in this embodiment the inner needle 302 does not require to be rotatable within the outer needle 306. In particular, the optical element 308 is arranged at the same side portion of the inner needle 302 as the receptacle 304. In this way, the inner needle 302 is not rotated to move between an imaging configuration and a sampling configuration in which the receptacle 304 is exposed.

For insertion of the biopsy needle 300 into tissue, the inner needle 302 is held within the outer needle 306 such that wall portions of the outer needle 306 cover the receptacle 304. A portion of the end cap 320 extends beyond the distal end 314 of the outer needle 306 so that a sharpened tip can be provided for the biopsy needle 300. The distal end 314 of the outer needle 306 is angled similar to the biopsy needle 200 shown in FIG. 2. Thereby, the optical element 308 can direct and receive light through the inlet 316 without the requirement for a further inlet within the outer needle 306.

As the biopsy needle 300 is inserted into the tissue, electromagnetic radiation is received from a tissue region that is located at the side portion of the biopsy needle 300. This received radiation may be used to form an image of the tissue region or to measure optical or mechanical properties of the tissue region such as an elasticity of the tissue region. It may also be used to detect when a blood vessel is adjacent to the biopsy needle 306.

Once the biopsy needle 300 has been inserted to a desired location within the tissue, the outer needle 306 is retracted allowing tissue to fill the receptacle 304. In particular, the outer needle 306 is translated relative to the inner needle 302. A rotation is not necessary to move to the sampling configuration. In addition, in accordance with this embodiment, the optical element 308 may continue receiving electromagnetic radiation while a tissue sample is obtained.

In some configurations, the inner needle 302 may be hollow such that suction can be created along the inner needle 302. This has the advantage that tissue can be aspirated into the receptacle 304.

The outer needle 306 is then extended once again over the inner needle 302 thereby obtaining the tissue sample within the receptacle 304 of the inner needle 302 by virtue of a cutting element located at an edge of the angled distal end 314 of the outer needle 306. The biopsy needle 300 can then be withdrawn from the tissue and the tissue sample can be removed from the receptacle 304 for further analysis.

This embodiment has the significant advantage that the optical element 308 can receive light whilst the tissue sample is received within the receptacle 304 and cut from surrounding tissue by virtue of the cutting element at the edge of the angled distal end 314 of the outer needle 306.

Referring now to FIG. 4, there are shown examples of optical elements that are arranged to direct electromagnetic radiation in a direction that is substantially perpendicular to a longitudinal axis of a needle in which the optical element is arranged. In particular, the optical elements are arranged within an inner portion of an inner needle such as inner needle 102, 202, 302. The optical elements typically comprise an optical fibre that establishes communication with a light source and/or an optical processing system, such as single-mode, multi-mode or double-clad fibre. In these particular examples, the optical fibre comprises a length of no-core optical fibre and a length of graded-index (GRIN) optical fibre spliced to a length of single-mode optical fibre (SMF). The combination of no-core and GRIN fibre acts as a lens shaping the light beam that is emitted into surrounding tissue.

Figure 4A:
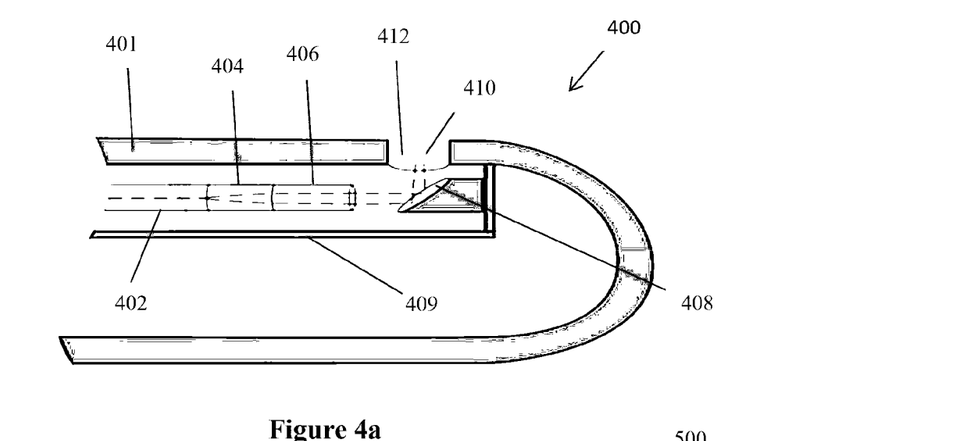
FIG. 4 shows schematic representations of exemplary optical elements.

FIG. 4a shows an optical element 400 that is incorporated into an inner needle 401. The optical element 400 comprises a single-mode optical fibre 402 which is attached at its distal end to a length of no-core fibre 404 to expand the light beam, followed by a length of GRIN fibre 406 with a pitch of approximately 0.16, to focus the light into the tissue. A person skilled in the art will appreciate that the working distance and spot size of the emitted light may for example be adjusted by varying the pitch of the GRIN fibre.

A small copper mirror 408 is positioned opposite the fibre 402, 404, 406 and polished at an angle of 45 degrees so that a light beam 410 is redirected at right angle. However, a person skilled in the art will appreciate that any suitable angle is envisaged. The optical fibre 402, 404, 406 and the mirror 408 need to be carefully aligned. In this case, both are positioned within a metal tube 409 to hold them rigidly in alignment within the inner needle 401. The needle 401 further comprises an inlet 412, such as inner inlets 116, 216 or 316, that is transmissive to the light 410 that is redirected from the mirror 408. The inlet 412 in this particular example is etched in the shaft of the inner needle 401 approximately 4 mm from the tip.

Figure 4B:
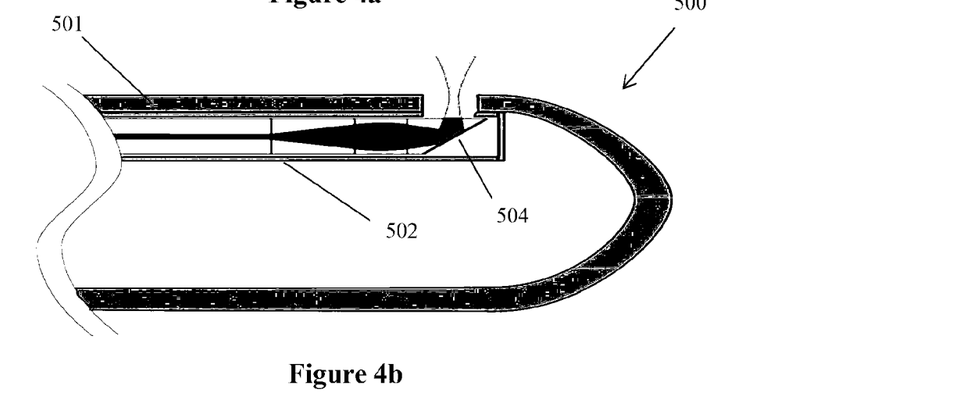

FIG. 4b shows a further example of an optical element 500 that is incorporated into an inner needle 501. Rather than providing a separate mirror at the tip of the distal end of the inner needle 501, the optical element 500 comprises a fibre 502 that terminates with an angled, reflection-coated piece of fibre 504. A person skilled in the art will appreciate that any suitable material for the angled, reflection-coated piece of fibre 504 may be used, for example multilayer dielectric coatings or reflective metals such as gold, silver, aluminium.

Figure 4C:
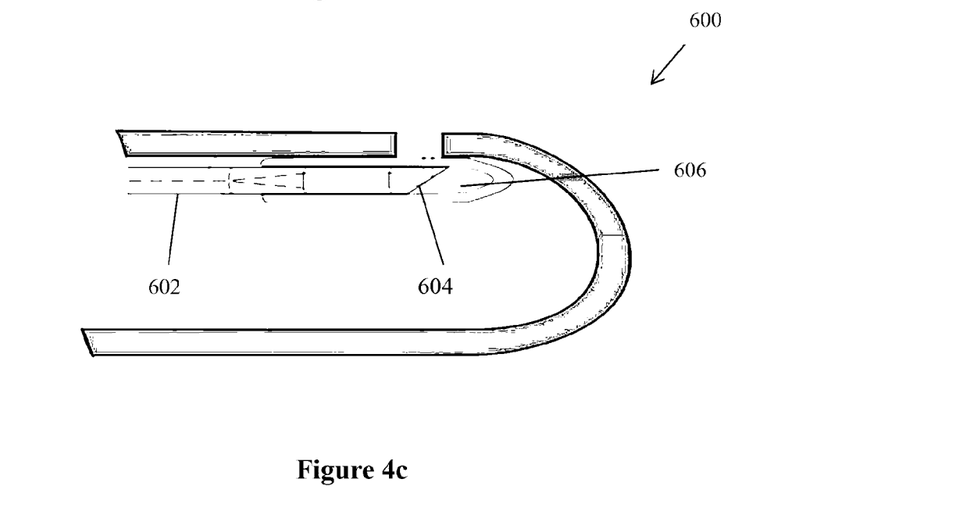

Referring now to FIG. 4c, there is shown a further alternative optical element 600 that is arranged to direct the light beam into the tissue. Instead of coating the angled fibre with metal as shown in FIG. 4b, the optical element 600 comprises an optical fibre 602 which has an angled distal end 604 made of glass. The distal end of the fibre 602 is enclosed in a hollow glass tube 606 (a capillary). The glass tube 606 captures an air bubble adjacent to the angled distal end 604. Light is then reflected via total internal reflection at the glass-air boundary. This is due to the fact that the refractive indices of glass and air are quite different, such that when a light beam is directed onto the surface of the angled distal end 604, it reflects at approximately 90 degrees instead of passing through the surface.

Figure 5A:
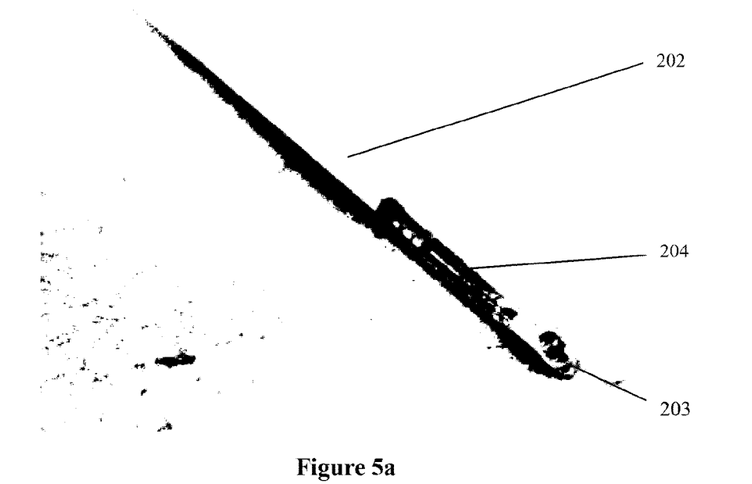
FIGS. 5a and b show photographs of the medical device of FIG. 2.
Figure 5B:
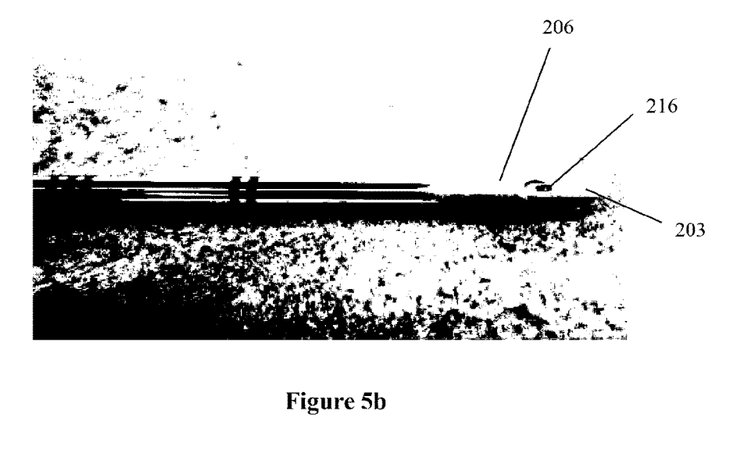
Figure 6:
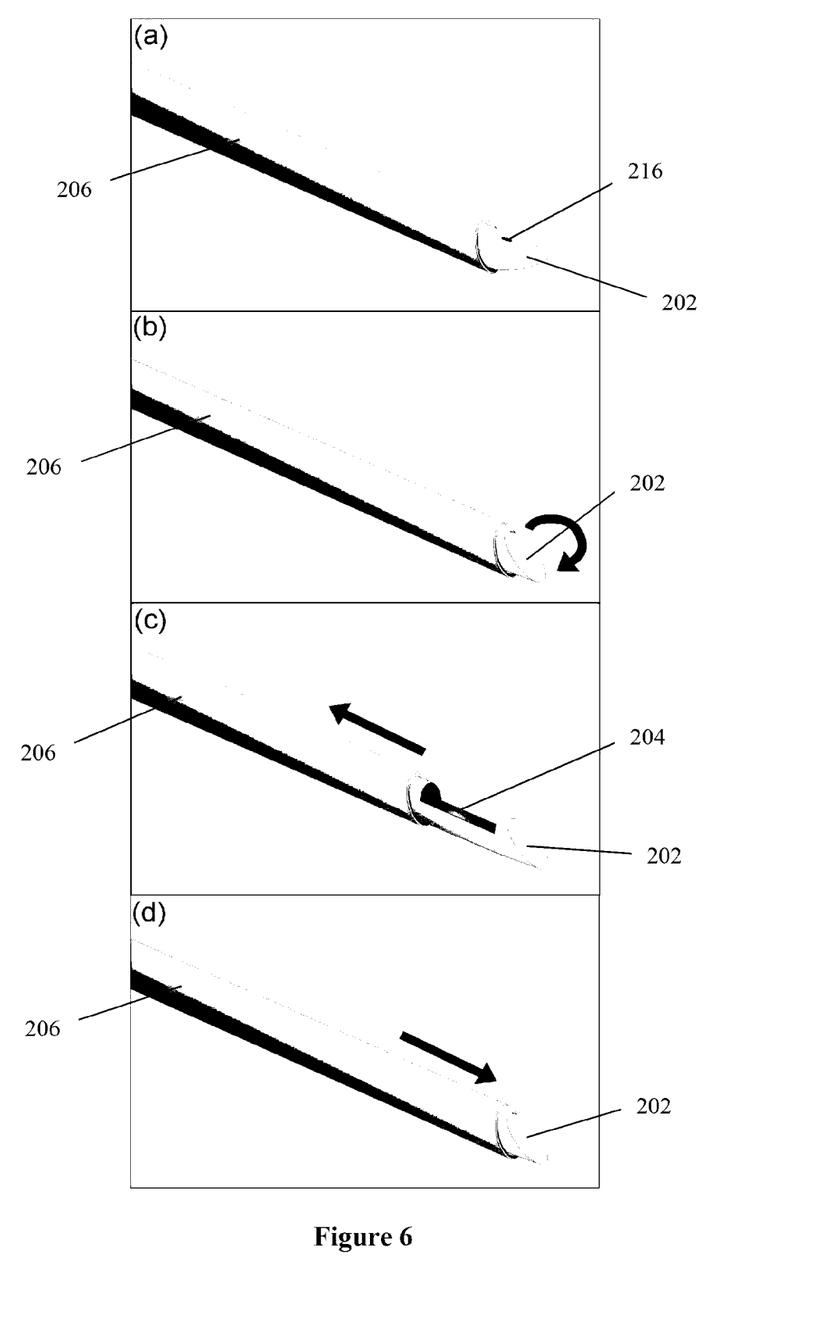
FIGS. 6a to d shows the medical device of FIG. 2 in different configurations illustrating operation of the medical device.
Figure 7:
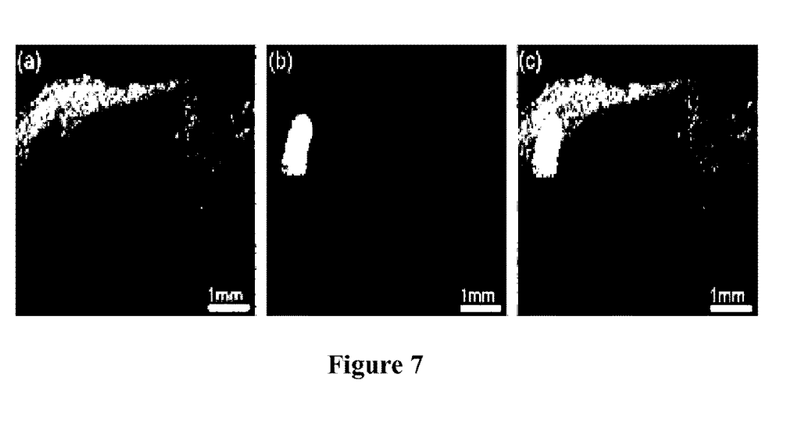
FIGS. 7 and 8 shows images generated from data acquired using the medical device of FIG. 2.

Referring now to FIGS. 5 to 7, additional information is provided with respect to the medical device 200 shown in FIG. 2.

FIGS. 5a and b show photographs of the biopsy needle 200 when manufactured following the design shown in FIG. 2. The biopsy needle 200 comprises a 16-gauge (OD 1.65 mm) inner needle 202 and a 14-gauge (2.11 mm) outer needle 206 with a length of 12 cm. FIG. 5a shows a photograph of the inner needle 202. As shown in the photograph, the inner needle 202 comprises the receptacle 204 for the tissue sample and the sharpened tip 203 for inserting into tissue. Further, the inner needle 202 has a hollow needle shaft through which the optical fibre 212 of the optical element 208 is threaded.

FIG. 5b shows a photograph of the inner needle 202 positioned within the outer needle 206 in imaging configuration. That is, the inner needle 202 has been rotated so as to expose the inlet 216. The inlet 216 is covered with a glass window through which near infrared light may be transmitted and received but which is impermeable to tissue. In this imaging configuration, the receptacle 204 is occluded by the outer needle 206. In this particular example, the receptacle 204 is located on substantially the opposite side on the inner needle 202 to the inlet 216.

Referring now to FIGS. 6a to d, there is shown different configurations of the biopsy needle 200 to illustrate the operation of the medical device 200. Initially, the distal end of the biopsy needle 200 is inserted into the tissue whilst in imaging configuration. In this particular example, in the imaging configuration as shown in FIG. 6a, the inner needle 202 is positioned relative to the outer needle 206 such that surrounding tissue can be imaged through the inlet 216 in order to detect any nearby blood vessels and to identify an optimal tissue sample for biopsy.

Once the biopsy needle 200 is positioned at the location where a tissue sample is to be obtained, the inner needle 202 is rotated by approximately 180 degrees relative to the outer needle 206. In this configuration as shown in FIG. 6b, the inlet 216 becomes occluded by the outer needle 206. The outer needle 206 is then retracted to move the biopsy needle into the sampling configuration as shown in FIG. 6c. In the sampling configuration, the receptacle 204 for receiving the tissue sample is exposed. Once tissue fills the receptacle 204 (possibly aided by applying suction through the hollow inner shaft of the inner needle 202), the outer needle 206 is extended again to occlude the receptacle 204 and cut the tissue sample inside of it as shown in the configuration in FIG. 6d. The inner needle 202 may then be withdrawn to extract the tissue sample whilst leaving the outer needle 206 in place. Alternatively, both the inner and outer needles 202, 206 may be withdrawn from the tissue.

A number of in vivo experiments have been completed with the biopsy needle 200 shown in the photographs in FIGS. 5a and b to assess its ability to detect blood vessels in biological tissue adjacent to the biopsy needle 200. An optical coherence tomography (OCT) fibre-probe was affixed inside the inner needle 204. The fibre-probe used the optical design described in Scolaro, L., et al., *High-sensitivity anastigmatic imaging needle for optical coherence tomography*. Optics Letters, 2012. 37(24): p. 5247-5249 which is herein incorporated in its entirety by reference. The fibre-probe was positioned so as to perform imaging through the inlet 216. The proximal end of the fibre-probe was connected to an OCT scanner, with a swept-source laser with a sweep rate of 36 kHz and an average output power of 30 mW. The system had an axial resolution of 6.8 µm (i.e. spatial resolution in the direction that the light beam is emitted from the biopsy needle 200).

The biopsy needle 200 was inserted into two NIH nude rats (NIHRNU-M) that had been anaesthetised with isoflurane. The insertion point was adjacent to the femoral artery. FIG. 7 shows imaging data acquired using the biopsy needle 200. FIG. 7(a) shows the OCT image acquired by the probe as the distal end of the biopsy needle 200 is inserted into the tissue. Relative to the image, the biopsy needle 200 is inserted horizontally, travelling from left to right. FIG. 7(b) shows a cross-sectional view of the femoral artery (white), which was automatically detected from the OCT image data using a blood vessel detection algorithm described in Lee, A. M. D., et al., *In vivo lung microvasculature visualized in three dimensions using fiber-optic color Doppler optical coherence tomography*. Journal of Biomedical Optics, 2013. 18(5): p. 050501 which is herein incorporated in its entirety by reference. FIG. 4(c) shows the detected femoral artery overlaid on the original OCT data.

Figure 8:
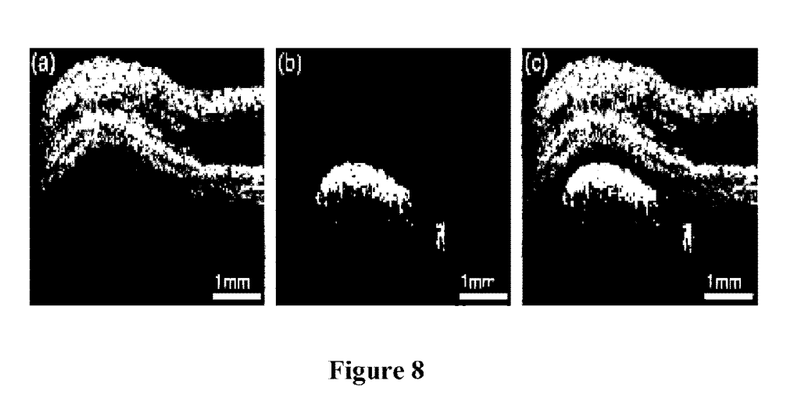

FIG. 8 shows imaging data of inserting the biopsy needle 200 into a second rat. The OCT image acquired with the fibre-probe is shown in FIG. 8(a). FIG. 8(b) shows a blood vessel (white) automatically detected from the OCT data. FIG. 8(c) shows the blood vessel overlaid on the OCT image.

Figure 9:
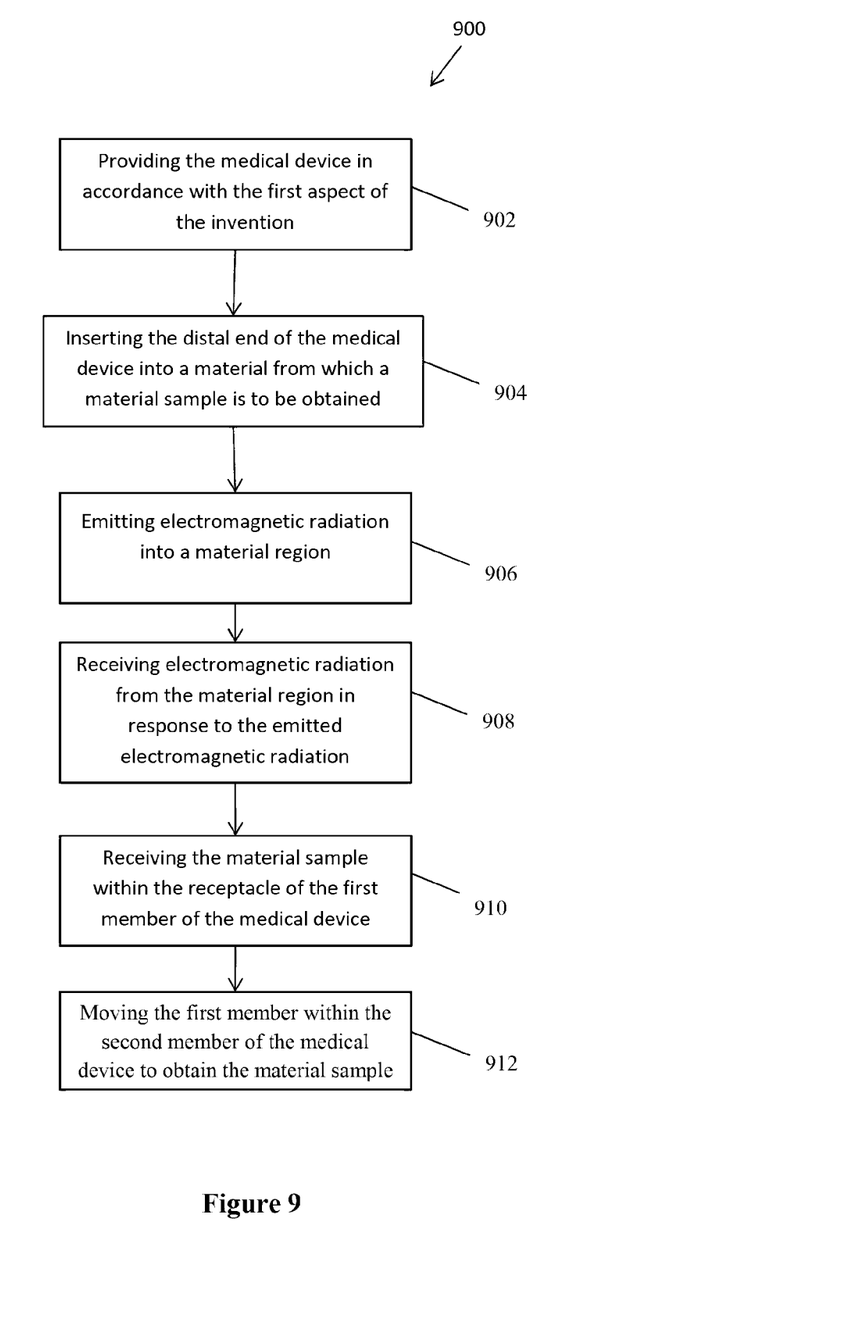
FIG. 9 is a flow chart of a method in accordance with an embodiment of the present invention.

FIG. 9 shows a flow diagram of a method 900 for inserting a medical device into a material to obtain a material sample in accordance with an embodiment of the present invention. In a first step 902, the medical device is provided such as one of the biopsy needles illustrated in FIGS. 1, 2 and 3. In a second step 904, the medical device is inserted into the material from which a material sample is to be obtained. In case of using a biopsy needle, the material typically is biological tissue in an organ such a brain, breast or prostate. However, other materials are envisaged. Electromagnetic radiation such as near-infrared light is emitted into the tissue in step 906. The electromagnetic radiation may be emitted into any suitable direction or directions. For example, if the medical device is an elongate biopsy needle, the electromagnetic radiation may be emitted in a direction parallel to the central axis of the biopsy needle. In response, a portion of the emitted electromagnetic radiation interacts with the tissue and electromagnetic radiation is received by the medical device (step 908). For example, the medical device may receive electromagnetic radiation that is backscattered by the tissue. As another example, the electromagnetic radiation emitted in step 906 may stimulate fluorescent emission from the tissue, and the fluorescent electromagnetic radiation may be received by the medical device. The electromagnetic radiation that is received in step 908 is usable to obtain information in relation to the material. For example, an elasticity of the material may be characterised. In a next step 910, the material sample is received in the receptacle of the medical device, for example by applying suction to the first member. In step 912 the material sample is obtained by moving the first member within the second member of the medical device.

The method 900 may further comprise a step of configuring the medical device from an imaging configuration in which the electromagnetic radiation is emitted and received to a sampling configuration in which the material sample is obtained. This step may be conducted by rotating and/or translating the first member of the medical device within the second member.

The step of obtaining the material sample 910 may comprise a step of cutting the material sample from surrounding material. The step of cutting the material may comprise rotating and/or translating the second member relative to the first member.

The method typically comprises a step of analysing the received electromagnetic radiation. For example, the received electromagnetic radiation may be analysed by a suitable imaging technique such as optical coherence tomography and/or fluorescence microscopy. Based on the analysis of the received electromagnetic radiation, a desired material sample may be located.

Although the invention has been described with reference to particular examples, it will be appreciated by those skilled in the art that the invention may be embodied in many other forms.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The claims defining the invention are as follows:

1. A medical device for obtaining a material sample from a material, the medical device comprising:
 a first member comprising a receptacle;
 a second member having a hollow region for accommodating at least a portion of the first member such that the at least a portion of the first member is movable within the second member and having an aperture through which in use the material sample is received, the second member further comprising an inlet that is transmissive for at least electromagnetic radiation that can be used to determine information in relation to the material, the aperture and the inlet being spaced apart from each other;

an optical element arranged to receive electromagnetic radiation from the material when the medical device is inserted into the material;

wherein the first member is rotatable within the second member to move between an imaging configuration in which the optical element receives the electromagnetic radiation through the inlet from the material, and a sampling configuration in which the material sample is received through the aperture into the receptacle when the medical device is inserted into the material, such that when the first member is in the imaging configuration, a portion of the second member covers the receptacle of the first member, and wherein the first member and the second member are arranged such that, when the material sample is received through the aperture and the first member is in the sampling configuration, the material sample can be obtained from the material within the receptacle by rotating the first member and the second member relative to each other.

2. The medical device of claim 1 being arranged such that the electromagnetic radiation from which the information relating to the material can be determined is captured in front of the aperture when the medical device is advanced into the material.

3. The medical device of claim 1 being arranged such that the optical element receives the electromagnetic radiation through the inlet from a direction that is parallel to a longitudinal axis of the medical device.

4. The medical device of claim 1 being arranged such that the optical element receives the electromagnetic radiation through the inlet from a direction that is perpendicular to a longitudinal axis of the medical device.

5. The medical device of claim 1, wherein the optical element is arranged to direct electromagnetic radiation into the material.

6. The medical device of claim 5 wherein the electromagnetic radiation is infrared light.

7. The medical device of claim 1 wherein the first member is rotated within the second member about 180 degrees to move between the imaging configuration and the sampling configuration.

8. The medical device of claim 1, wherein the inlet is arranged distally relative to the aperture of the second member when the medical device is inserted into the material.

9. The medical device of claim 8, wherein the inlet is arranged at or within a tip of a distal end of the medical device.

10. The medical device of claim 1, wherein the inlet is formed by a tip of a distal end of the medical device.

11. The medical device of claim 1, wherein the inlet comprises at least one inner inlet in the first member and/or at least one outer inlet in the second member.

12. The medical device of claim 1, wherein a distal end of the second member comprises a plurality of outer inlets and wherein the optical element is moveable relative to the second member such that electromagnetic radiation can be directed to and/or received from more than one outer inlet.

13. The medical device of claim 1, wherein the optical element is arranged within an inner portion of the first member.

14. The medical device of claim 1, wherein the inlet comprises an inner inlet arranged at a distal end of the first member, the inner inlet being arranged opposite to a receptacle of the first member.

15. The medical device of claim 1, wherein the first member also comprises an inlet that is transmissive for at least electromagnetic radiation that can be used to determine information in relation to the material, and the inlet of the second member and the inlet of the first member are aligned to allow transmission of the electromagnetic radiation through the inlet of the first member and the inlet of the second member only when the first member is rotated within the second member to the imaging configuration.

16. A method of obtaining a material sample from a material, the method comprising the steps of:
providing the material;
providing a medical device, the medical device having a first member and a second member, the first member comprising a receptacle and being positioned at least partially within the second member, the second member having an aperture through which in use the material sample is received, the second member further having an inlet that is transmissive for at least electromagnetic radiation that can be used to determine information in relation to the material, the aperture and the inlet being spaced apart from each other, and the first member being further rotatable within the second member to move between an imaging configuration in which the electromagnetic radiation can be emitted towards the material and received from the material through the inlet when the medical device is inserted into the material, and a sampling configuration into which the material sample is received through the aperture in the receptacle when the medical device is inserted into the material, such that when the first member is in the imaging configuration, a portion of the second member covers the receptacle of the first member;
inserting a distal end of the medical device into the material;
emitting electromagnetic radiation into the material;
receiving electromagnetic radiation from the material through the inlet in response to electromagnetic radiation emitted into the material;
rotating the first member within the second member between the imaging configuration and the sampling configuration;
receiving the material sample through the aperture of the second member when the first member is in the sampling configuration; and
rotating the first member and the second member relative to each other to obtain the material sample from the material within the receptacle.

17. The method of claim 16 being conducted such that the electromagnetic radiation from which the information relating to the material can be determined is captured in front of the aperture when the medical device is advanced into the material.

18. The method of claim 16 further comprising a step of analyzing the electromagnetic radiation received in response to electromagnetic radiation emitted into the material.

19. A method of obtaining a material sample from a material, the method comprising the steps of:
providing the material;
providing a medical device in accordance with claim 5;

inserting a distal end of the medical device into the material;

emitting electromagnetic radiation into the material;

receiving electromagnetic radiation through the inlet of the second member in response to electromagnetic radiation emitted into the material;

receiving the material sample through the aperture of the second member; and rotating the first member and the second member relative to each other to obtain the material sample from the material.

20. A medical device for obtaining a material sample from a material, the medical device comprising:

a first member having an aperture through which in use the material sample is received and further comprising an inlet that is transmissive for at least electromagnetic radiation that can be used to determine information in relation to the material, the aperture and the inlet being spaced apart from each other and being positioned at opposite sides or angular positions of the first member;

a second member having a hollow region for accommodating at least a portion of the first member such that the at least a portion of the first member is movable within the second member, the second member having an open distal end;

an optical element arranged to receive the electromagnetic radiation from the material when the medical device is inserted into the material;

wherein the first member is rotatable within the second member to move between an imaging configuration in which the optical element receives the electromagnetic radiation from the material through the inlet, and a sampling configuration in which the material sample is received through the aperture, such that when the first member is in the imaging configuration, a portion of the second member covers the aperture of the first member, and wherein the first member and the second member are arranged such that, when the medical device is in a condition for receiving the material sample, a distal end of the first member penetrates through the open distal end of the second member and the material sample, when received through the aperture of the first member, can be obtained from the material by rotating the first member and the second member relative to each other.

* * * * *